United States Patent [19]

De Antoniis et al.

[11] Patent Number: 4,714,769

[45] Date of Patent: Dec. 22, 1987

[54] PROCESS FOR THE SYNTHESIS OF ORGANOFUNCTIONAL SILANES USING ISATOIC ANHYDRIDE OR DERIVATIVES THEREOF

[75] Inventors: Mario De Antoniis, Monterotondo; Mario Fiorini; Giuseppina Mazzamurro, both of Rome, all of Italy

[73] Assignee: Eniricerche S.p.A., Milan, Italy

[21] Appl. No.: 877,900

[22] Filed: Jun. 24, 1986

[30] Foreign Application Priority Data

Jul. 1, 1985 [IT] Italy ................................ 21374 A/85

[51] Int. Cl.$^4$ .......................... C07F 7/10; B32B 27/36; B32B 9/00; B32B 17/06
[52] U.S. Cl. ...................................... 556/419; 428/46; 428/412; 428/429; 428/447; 428/474.4; 428/480; 428/500; 428/522; 428/523; 428/532; 428/704; 106/287.11
[58] Field of Search .................. 556/419; 106/287.11; 428/46, 429, 412, 480, 447, 474.4, 532, 704, 560, 522, 523

[56] References Cited

U.S. PATENT DOCUMENTS

| | | | |
|---|---|---|---|
| 2,929,829 | 3/1960 | Morehouse | 556/419 |
| 3,455,940 | 7/1969 | Stecker | 556/419 X |
| 4,328,216 | 5/1982 | Toyoshima et al. | 556/419 X |

Primary Examiner—Paul F. Shaver
Attorney, Agent, or Firm—Hedman, Gibson, Costigan & Hoare

[57] ABSTRACT

A process for the synthesis of organofunctional silanes having general formula (I), as well as the use of them is disclosed.

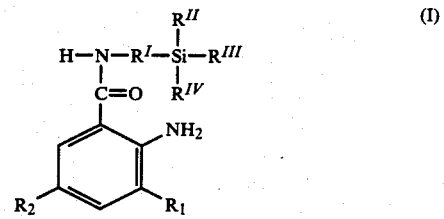

10 Claims, No Drawings

PROCESS FOR THE SYNTHESIS OF ORGANOFUNCTIONAL SILANES USING ISATOIC ANHYDRIDE OR DERIVATIVES THEREOF

The present invention relates to a process for the synthesis of organofunctional silanes having the general formula (I)

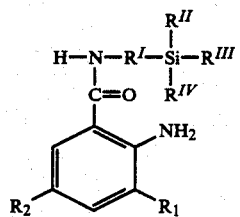

wherein
$R_1$, $R_2$, are equal to or different from each other = Cl, Br, $CH_3$, $NO_2$, H, $NH_2$;
$R^{II}$, $R^{III}$, $R^{IV}$, are equal to or different from each other, are alkyl or alkoxy groups containing from 1 to 10 carbon atoms;
$R^I$, can be an alkyl, aminoalkyl, aminoalkylaryl or alkylaryl group containing from 1 to 10 carbon atoms.

The present invention relates also to the use of these compounds in particular applications.

From the technical literature, different methods are known for the synthesis of organofunctional silanes (Silane Coupling Agents, by E. P. Plueddemann, Plenum Press, 1982; Silicated Surfaces, by D. E. Leyden and W. Collins, Gordon & Breach Science Publishers, 1980); for example, benzamide-4-amino-N-3-triethoxysilylpropyl can be synthetized by a step process, which can be schematically shown as follows:

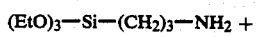

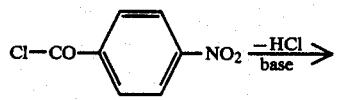

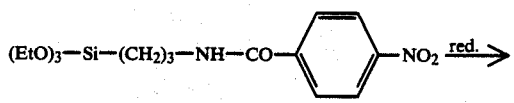

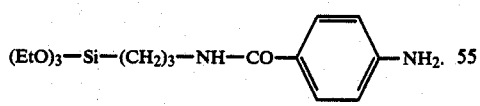

Such a method could be used also for the synthesis of

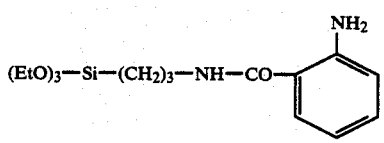

by using as reactants:

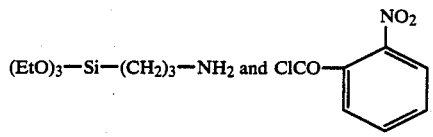

As a matter of fact, it must be observed that such synthesis processes as those described above have never been actually tested in homogeneous phase, but in heterogeneous phase only, viz., after having fixed aminopropyltriethoxysilane on solid matrices.

Our process, which to the contrary allows the silanes discussed to be synthetised in homogeneous phase, as it shall be disclosed hereunder, is clearly preferable; furthermore, even by carrying out the synthesis in homogeneous phase of the silanes with the aminic group in para-position, one would have, relative to what is herein claimed, one more reaction and hence lower overall yields, longer times and higher costs.

Going back to the object of the present invention, we have found that it is possible to synthesize organofunctional silanes of general formula (I) by a simplified process, which gives quantitative yields, and wherein isatoic anhydride (2H-3.1-benzoxazine-2,4-(1H)diene) and/or derivatives thereof with substituents on the benzenic rings are used.

An object of the present invention is therefore a process for the synthesis of organofunctional silanes having general formula (I)

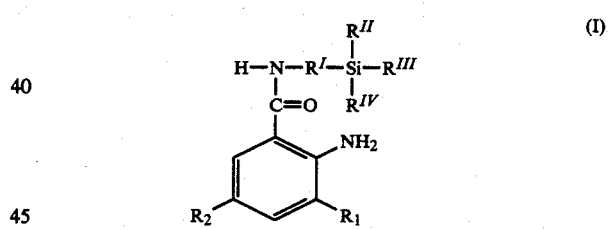

wherein
$R_1$, $R_2$, are equal to or different from each other = Cl, Br, $CH_3$, $NO_2$, H, $NH_2$;
$R^{II}$, $R^{III}$, $R^{IV}$ are equal to or different from each other, are alkyl or alkoxy groups containing from 1 to 10 carbon atoms;
$R^I$, can be an alkyl, aminoalkyl, aminoalkylaryl or alkylaryl group containing from 1 to 10 carbon atoms.

According to this process, isatoic anhydride, or its derivatives, and aminosilanes of

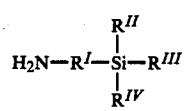

type, are reacted according to the following reaction diagram:

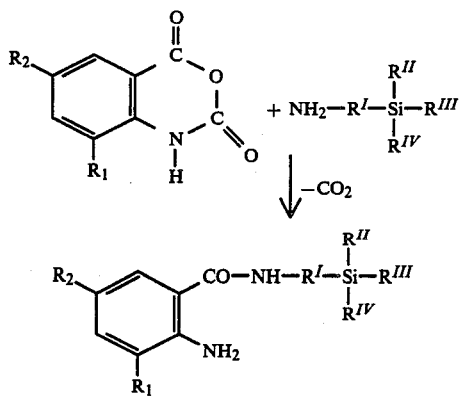

In particular, the synthesis is disclosed of benzamide-2-amino-N-3-triethoxysilylpropyl, having the following formula:

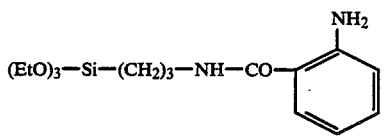

which is not described in the technical literature, and is hence a further object of the present invention.

The silanes practically preferred according to the purposes of the present invention are:

3-aminopropyltriethoxysilane
$H_2N-(CH_2)_3-Si-(OC_2H_5)_3$
aminomethyltriethoxysilane
$H_2N-CH_2-Si-(OC_2H_5)_3$
2-aminoethyl-aminopropyltrimethoxysilane
$H_2N-(CH_2)_2-NH-(CH_2)_3-Si(OCH_3)_3$
2-aminoethylaminopropyltriethoxysilane
$H_2N-(CH_2)_2-NH-(CH_2)_3-Si(OC_2H_5)_3$
2-aminoethylaminopropylmethyldimethoxysilane

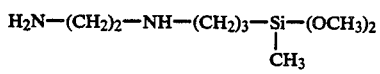

The reaction synthesis is carried out by gradually adding isatoic anhydride to the aminosilane either in the presence or in the absence of solvent. By carrying out the reaction in a solvent, it is obviously necessary that this latter be not reactive with isatoic anhydride; in case of hydroxylated solvents, it shall be necessary to use, e.g., mild reaction conditions, and operate in the absence of possible catalysts. However, solvents, alcohols, ethers, chlorinated solvents, and so forth, can be used. Of course, operating is necessary in the absence of water, which would cause alkoxy groups to hydrolize.

The reaction can also be carried out by adding isatoic anhydride all together, by taking in the due account the slight exothermicity of the reaction (cooling shall be necessary) and that, notwithstanding the considerable difference in reactivity between the aliphatic amine (aminosilane) and the aromatic amine (reaction products), oligomeric products of type

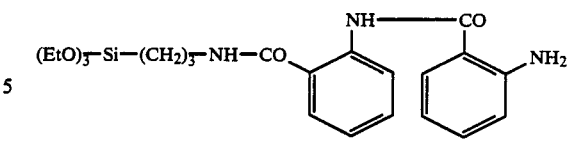

could be formed, even if in very minor amounts.

As regards the reaction to be carried out in the absence of solvent, one should keep in mind that in this case a good stirring and a cood $CO_2$ stripping system are necessary, and that operating in this way is possible only if the end product is liquid.

The organofunctional silanes of the present invention find application in many fields. First of all, their use is in compositions for use as thermosetting paints, to obtain clear coatings uniform and resistant to solvents—and to which, to the purpose of increasing their resistance to abrasion and solvents, other organofunctional silanes can be added.

Such coatings are useful to coat and protect such soft substrates as the organic polymers, to which such coatings are bonded by direct adhesion. The compositions are finished by a diluent solvent and an acid; they are applied onto the surface of the substrates, and thermoset, to form insoluble coatings strongly bonded to said substrates.

Such coatings confer to the substrates compatibility and characteristics of adhesion to further coatings, thus making it possible to obtain useful multilayer manufactures, which, should such a coating be absent, could not be obtained by direct adhesion.

The useful organic polymers are: aromatic polycarbonates, aliphatic polycarbonates, polyacrylates, polymethacrylates, polyesters, cellulose esters, polyacetates, polyamides, polyvinylchloride, polysulphone, polyethersulphone, polystyrene and copolymers of styrene with acrylonitrile and acrylonitrile-butadiene.

The compounds having formula (I) can be useful in very many other fields, wherein surface modifications of solid matrices are required.

In general, one can say that the surfaces of the oxides (or of metals the surfaces of which are usually oxidized) can be modified with organofunctional silanes to make them fit to be used in fields very different to each other, such as heterogeneous catalyses (immobilization of homogeneous catalysts), separation of organic substances by chromatography, research on electrodes, immobilization of dyes, besides the more generalized field of the manufacturing of composite materials, process in which the organofunctional silanes are used as coupling agents. A specific example of these possibilities relates to the immobilization of chelating agents on siliceous surfaces to yield products for use in different processes, such as, e.g., the separation or concentration of metal ions.

The immobilization of chelating agents on siliceous matrices, instead of using the traditional polymeric resins, yields advantages derived from a greater mechanical stability, possibility of use under more severe conditions and higher kinetics.

In case the chelating agent 8-Quinolinol is fixed on silica, usually p-aminophenyltrimethoxysilane is used [Anal. Chem. 55, 2089 (1983), U.S. Pat. No. 3,886.080; however, the use of composite p-aminophenyltrimethoxysilane involves difficulties derived from the incomplete use of the exchange capacity of the chelating agent, mainly because the commercial product is constituted by a mixture of the three isomers, and the aromatic group is very close to the siliceous surface, causing a steric hindrance (Anal. Chem. 57, 375, (1985)). These problems can be overcome either by following the classic immobilization method, which involves the synthesis in heterogeneous phase of benzamide-4-amino-N-3-trioxysilylpropyl, or by using benzamide-2-amino-N-3-triethoxysilylpropyl synthesized by us according to our process.

The normal immobilization procedure is the following:

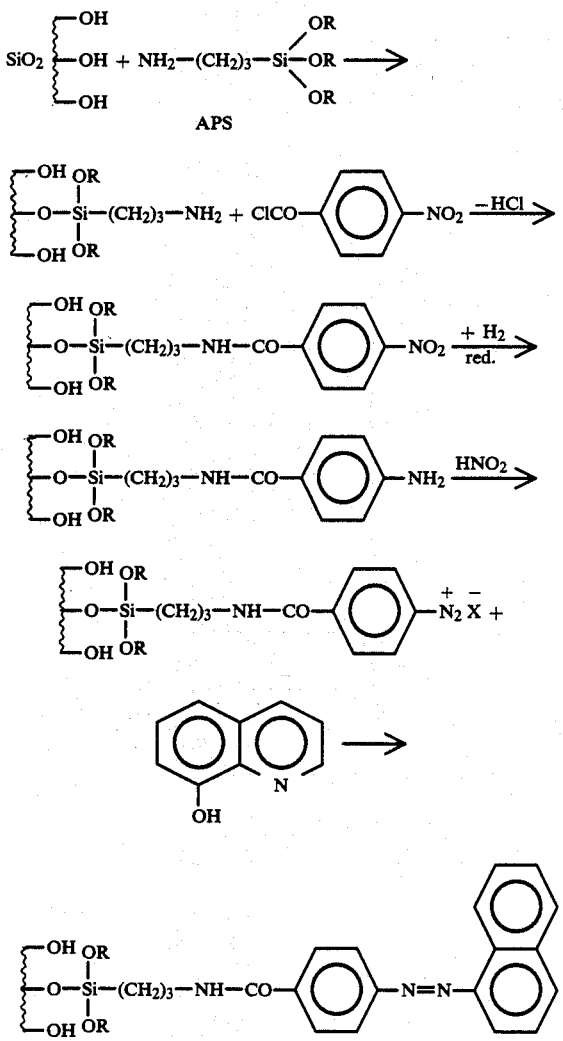

The main drawback is the high number of chemical reactions in heterogeneous phase; some of these are very long and their yields are not very high. This leads to an end product the capacity of which, per unit weight, besides being already low due to steric hindrance problems, caused by the silica structure, is furthermore decreased relative to the number of groups functionalized in the first reaction. Notwithstanding all the various steps have been widely studied and optimized (Anal. Chim. Acta 129, 29–47, 1981), some alternatives have been proposed for the purpose of reducing the complexity of the system.

Mottola H. A. et al. (Anal. Chem. 55, 2089–2093, 1983) have proposed the use of aminophenyltrimethoxysilane, which has the evident advantage of being suitable to be directly diazotized and coupled with the chelating agent.

Besides the considerable cost of the product, the problems exist of great steric hindrance due to the absence of a spacer group interplaced between the silicon atom and the aromatic ring, and to the consequent relative closeness of the aminic group to the siliceous matrix; this problem is made worse by the fact that the commercial product is constituted by a mixture of the three isomers.

Another improvement proposed (Tolonta 32, 813, 763–770, 1985) is that of synthesizing the compound

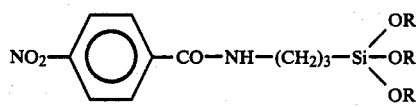

in homogeneous phase, rather than carrying out the reaction in heterogeneous phase; it shall be clear how in this case too, the advantages are really not substantial.

In the technical literature (Fres. Z. Anal. Chem. 322, 47–52, 1985) other proposals exist, but which actually do not solve the problem of the complexity of silica functionalization.

The global system tested by us is schematically shown as follows:

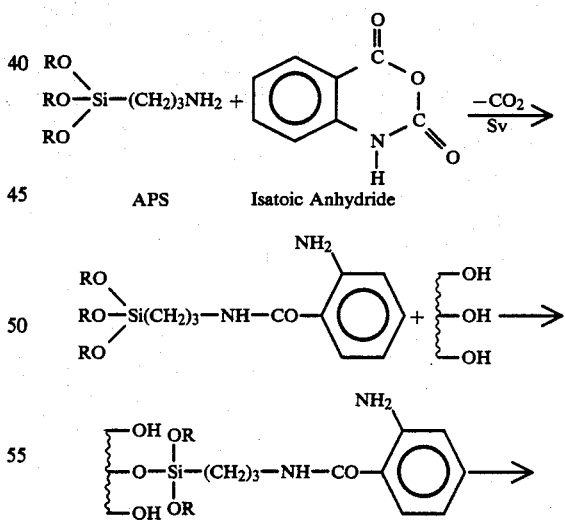

(as in preceding reaction scheme).

The advantages derived from the use of such compounds are evident, while the possibility should be underlined of a possible reduction of activity, deriving from the ortho-position of the amino group relative to the amido group, due to steric hindrance, as well as other possible drawbacks derived from side reactions.

To complete this survey, we note how the chelating power, or, better, the reactivity of silica is strongly determined, with the functionalizing procedure and the operating conditions being the same, by the type of silica, and the activation thereof (Anal. Chim. Acta 158, 369–373, 1984).

EXAMPLE 1

Into 100-ml glass flask, 30 ml of ethyl ether and 7 ml (29.84 mmol) of aminopropyltriethoxysilane (product by Fluka) are charged. Under stirring, and under nitrogen atmosphere, 4.86 g (29.84 mmol) of isatoic anhydride (product by Fluka) is gradually added, over a total time of 45 minutes.

During the addition, and also after the addition thereof ($\approx$15 minutes), the evolution of $CO_2$ is observed very clearly, by a bubble-flowmeter. At the end of the same reaction, a solution of yellowish colour is obtained which, after being concentrated in vacuo ($\approx$5 mm$_{Hg}$), yields a very viscous liquid of brown-red colour. This liquid is submitted to distillation by a diffusion pump equipped with vacuum gauge.

At a temperature of 164° C., under a vacuum of $\approx 10^{-5}$ mm$_{HG}$, a product is distilled which, under normal conditions, is a solid with a melting point of $\approx$35° C. The compound collected corresponds to 8.3 g.

An aliquot of this product is submitted to N.M.R. analysis, using deuterochloroform as the solvent. The resulting spectrum is in accordance with the proposed structure, and more precisely is composed by the following signals:

$\delta$0.645 multiplet 2H, $CH_2$—Si; 1.18 triplet 9H, $CH_3$; 1.70 multiplet 2H, $CH_2$—$CH_2$—$CH_2$; 3.32 multiplet 2H, $\underline{CH_2}$—N; 3.76 quadruplet 6H, $CH_2O$; 5.76 broad 2H, $NH_2$; 6.40–7.50 5H, $\phi$, NHCO. Also I.R. and mass-spectrometry spectra are in accordance with the proposed structure.

EXAMPLE 2

The same experimental test as of Example 1 is repeated, but using ethyl alcohol as the solvent, and the same product being obtained in the amount of 7.92 g.

EXAMPLE 3

Into a 100-ml three-necked flask, the following products (commercial products by Fluka) are charged under nitrogen atmosphere:
(I) Aminopropyltriethoxysilane 7 ml (APS)
(II) Trimethoxymethylsilane 17.4 ml (MTS)
Absolute ethyl alcohol 10 ml These amounts of silanes correspond to an APS/MTS (I/II) molar ratio of ¼.

To this solution 4.89 g of isatoic anhydride is gradually added under stirring. At the end of the addition, and at the end of $CO_2$ evolution, 1.36 ml of $H_2O$, 2 ml of acetic acid, and 8 ml of absolute ethyl alcohol are added, an end solution with pH$\approx$4 being obtained. This solution is kept stirred 2 days, and is then filtered on a 3$\mu$ filter.

The amount of water introduced into the solution corresponds to that necessary to hydrolyze 1/6 of total alkoxy groups of the two silanes.

EXAMPLE 4

A solution analogous to the foregoing Example 3 and obtained in the same way is prepared, with the only difference that APS/MTS ratio is=1/1.

The amount of water added corresponds this time to 1/10 of the total alkoxy groups.

EXAMPLE 5

The compositions obtained according to Examples 3 and 4 have been used to paint samples of polycarbonate shaped as square slabs with a side of 15 cm, and of 3 mm in thickness, obtained by injection moulding the commercial material SINVET 251/01. The painting has been carried out 2 days and 20 days later than the preparation date, no differences in performance being observed as for the relevant characteristics (adhesion, resistance to $H_2O$, etc.).

The specimens have been painted at 20° C., inside a chamber maintained at a relative humidity of 28%, by the dipping technique, the specimens being moved at the speed of 115 cm/min.

Each specimen has been left 15 minutes under air, and has been then oven-cooked at 120° C. for 90 minutes. Coatings having thickness ranging from 2 to 5 microns are so obtained.

To comparative purposes, by the same modalities specimens have been painted with solutions having the same concentration of silane, and of the other components of the solution ($H_2O$, $CH_3COOH$, EtOH), by using methyltrimethoxysilane (MTS) and aminopropyltriethoxysilane as the silane components (compositions 5 and 6).

On the painted specimens the properties of the coatings, and more precisely the transmittance, the adhesion, the abrasion resistance and the resistance to acetone have been tested.

The transmittance has been measured by using a GAR-DENER HAZEMETER.

The adhesion to the substrates has been measured by cutting on the surface 100 squares of 1 mm in side, wherein the depth of the cuts are higher than the coatings thickness. On the cut squares, a section of adhesive tape type "Scotch" Brand Magic Transparent Tape No. 810 (3M) was applied. After applying a strong pressure, the tape has been abruptly peeled away, by pulling at an angle of 90° relative to the specimen surface.

To the adhesion a rating comprised between 0 and 100 is thus given, as a function of the number of squares peeled away after three repeated tests.

The abrasion resistance has been determined according to ASTM D1044, by a TABER abrasion meter, using CS-10F grinding wheels under a 500 g load, and measuring the increase in HAZE as a function of the number of cycles.

The resistance to acetone is evaluated by applying onto the surface an absorbent cotton pad soaked with solvent, and verifying the presence of possible spots of attack.

The results are displayed as a function of the different properties.

(A) Adhesion

As for the adhesion soon after the painting, none of samples prepared show peelings. To the contrary, after the test of resistance in hot water at 80° C., samples 5 and 6 show peelings of the order of 50% after 12 hours, while samples 3 and 4 have much higher performance as for such a resistance.

More precisely, sample 3 shows peelings lower than 4% after 15 days in $H_2O$ at 80° C.; sample 4 does not show any attack after 18 days in $H_2O$ at 80° C.

(B) Abrasion Resistance

The values of HAZE are reported of polycarbonate "as such" (Pc), and Samples 3 and 4, as a function of the cycle number.

|  | Number of Cycles | HAZE |
|---|---|---|
| Pc as such | 0 | 0,74 |
|  | 5 | 16.6 |
|  | 10 | 21.8 |
| Sample No. 3 | 0 | 1.3 |
|  | 5 | 3.1 |
|  | 10 | 4.5 |
|  | 15 | 6.2 |
|  | 20 | 7.0 |
|  | 25 | 8.2 |
|  | 35 | 11.2 |
|  | 45 | 13.3 |
|  | 55 | 15.2 |
|  | 65 | 16.2 |
| Sample No. 4 | 0 | 1.4 |
|  | 5 | 7.5 |
|  | 10 | 11.0 |
|  | 15 | 14.7 |
|  | 20 | 16.0 |
|  | 25 | 19.1 |

(C) Resistance to Attack by Acetone

While Pc "as such" is immediately attacked by acetone, samples 3 and 4 show only punctiform attacks after more than 5 minutes.

EXAMPLE 6

Immobilization of Chelating Agents (A) Reaction with silane

A1. Reaction with ATPS (Anthranylaminopropyltriethoxysilane.

Into a 250-ml flask 10 g of silica Merck 60, preliminarily kept 4 hours in oven at 100° C., and 50 cc of toluene dried by molecular sieves are introduced under nitrogen; ≈3 g of ATPS is then added. The reaction mixture is refluxed 4-5 hours. The silica is then filtered off, repeatedly washed with anhydrous toluene and ethanol, dried in oven at 100° C., and is then stored in a desiccator.

A2. Reaction with APS (Aminopropyltriethoxysilane).

The procedure is the same as of preceding S A1.

A2.1. Reaction with Isatoic Anhydride.

Product A2 (2 g) is charged into a 100-cc flask with 60 ml of tetrahydrofuran, then 2 g of isatoic anhydride is added, and the whole is reflxed under stirring, with a spherical bulb condenser. The reaction, differently to the analogous reaction in homogeneous phase, is considerably slower, as it can be seen from the evolution of $CO_2$ from the bubble meter. After three hours, the solid product is filtered off, is repeatedly washed with tetrahydrofuran, a further 50 ml of the same solvent is added, with an amount of n-propylamine slightly in excess relative to the initial amount of isotoic anhydride, for the purpose of removing unreacted anhydride. After the end of $CO_2$ evolution, the product is filtered off, is washed with tetrahydrofuran and ethanol, and is dried.

A3. Reaction with AEAPS (Aminoethylaminopropyltriethoxysilane)

First of all, the reaction is carried out between AEAPS and isatoic anhydride in equimolecular ratio (100 mmol), in 50 ml of tetrahydrofuran under $N_2$ for 4 hours. At the end of $CO_2$ evolution, 5 g is added of $SiO_2$, and the procedure as in the other cases is then followed.

(B) Reaction with Nitrous Acid

Into a 50-ml beaker, 1 g of silica functionalized with an aromatic amine, and the 30 ml of 2N HCl are added. Under stirring, and at the temperature of ≈5° C., an aqueous solution (1 g in 20 ml) is added of $NaNO_2$. Two hours after the addition of $NaNO_2$, the silica is washed three times with cold $H_2O$ (50 ml each time). Silicas having a more or less bright yellow colour, typical of diazonium salts, are unvariably obtained.

(C) Coupling Reactions

As said, the coupling reaction can take place at different pH values; in our case, with the exception of the situations wherein the diazotization and coupling reactions are carried out in one step only, in water-alcoholic solution due to the insolubility of 8-hydroxyquinoline in water, all the coupling reactions are carried out at pH of 8-hydroxyquinoline, both in a water-alcohol, and in an alcohol solution.

In a typical example, to the immobilized diazo salt freshly prepared (10 minutes), a large excess of solution of 8-hydroxyquinoline is added, the whole is made to react under stirring for about one hour, and then, after filtering, is repeatedly washed with 1N HCl, $H_2O$, ethanol and acetone, until from the filtrate the colour disappears.

In all the preparations, a deep purple colour has developed, qualitative indication of 8-hydroxyquinoline coupling.

(D) Chelation Tests

In a typical test, about 20 ml of a standard solution containing about 150 µg/ml of $Cu^{++}$ prepared from $CuSO_4.5H_2O$ in acetate buffer at pH≈5, are charged into a flask containing about 0.2 g of silica. The mass is kept agitated by a shaker about 1 hour (kinetic measurements have shown that this time is enough), and the silica is then filtered off. The measurement of the chelating capacity is carried out by using as the computation basis the difference in concentration between the standard solution and the filtrate. The measurements are carried out by atomic-absorption analysis. The chelating capacity of silica alone has also been measured, by being afraid that it could considerably influence the values found.

TABLE 1

| Sample | Chelating Capacity µmol of $Cu^{++}$/g of $SiO_2$ |
|---|---|
| 1 | 0.5 |
| 2 | 46 - Average of 3 tests |
| 2a | 91 - Average of 7 tests |
| 3 | 30 |
| 3a | 79 - Average of 5 tests |
| 4 | 31 |
| 4a | 36.5 - Average of 2 tests |

NOTES:
Sample 1 = $SiO_2$ Merck 60
Sample 2 = $SiO_2$ + homogeneous ATPS
Sample 2a = Sample 2 + 8-hydroxyquinoline
Sample 3 = $SiO_2$ + APS + Isatoic anhydride
Sample 3a = Sample 3 + 8-hydroxyquinoline
Sample 4 = $SiO_2$ + AEAPS
Sample 4a = Sample 4 + 8-hydroxyquinoline.

We claim:

1. Benzamide-2-amino-N-3-triethoxysilylpropyl.

2. A process for the synthesis of organofunctional silanes having the formula (I)

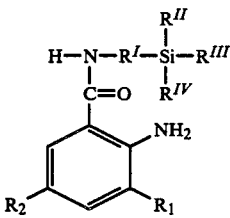

wherein
- R$_1$ and R$_2$ are equal to or different from each other and are selected from Cl, Br, CH$_3$, NO$_2$, H and NH$_2$;
- R$^{II}$, R$^{III}$, R$^{IV}$, an equal to or different from each other and are selected from alkyl and alkoxy groups containing from 1 to 10 carbon atoms;
- R$^I$ is selected from alkylene, aminoalkylene and aminoalkylarylene groups, said process comprising reacting isatoic anhydride or derivatives thereof represented by formula (II)

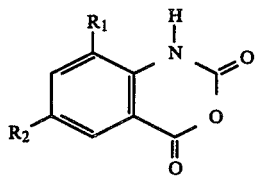

and aminosilanes of the formula (III)

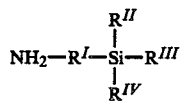

wherein each of R$_1$, R$_2$, R$^I$, R$^{II}$, R$^{III}$, R$^{IV}$, have the meaning set forth above.

3. The process according to claim 2, wherein the process is carried out in the presence of a solvent.

4. The process according to claim 3, wherein the solvent is selected from alcohols, chlorinated solvents, ethers and esters.

5. An organosiloxane composition useful as a protective abrasion-resistant and adhesion-promoting coating of organic polymers comprising at least one compound having the formula (I)

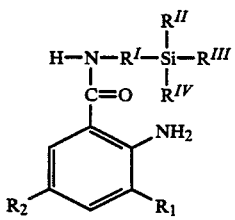

wherein
- R$_1$ and R$_2$ are equal to or different from each other and are selected from Cl, Br, CH$_3$, NO$_2$, H and NH$_2$;
- R$^{II}$, R$^{III}$, R$^{IV}$, an equal to or different from each other and are selected from alkyl and alkoxy groups containing from 1 to 10 carbon atoms; and
- R$^I$ is selected from alkylene, aminoalkylene and aminoalkylarylene groups.

6. The organosiloxane composition of claim 5 wherein the organic polymers are selected from aromatic polycarbonates, aliphatic polycarbonates, polyacrylates, polymethylacrylates polyesters, cellulose esters, polyacetates, polyamides, polyvinylchloride, polysulphone, polyethersulphone, polystyrene and copolymers of styrene with acrylonitrile and acrylonitrile-butadiene.

7. An article of manufacture comprising an organic polymer coated with at least one organo functional silane having the formula (I)

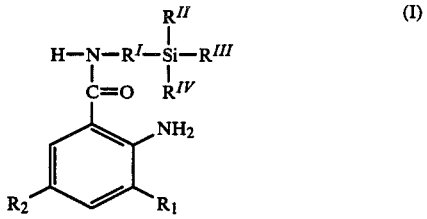

wherein
- R$_1$ and R$_2$ are equal to or different from each other and are selected from Cl, Br, CH$_3$, NO$_2$, H and NH$_2$;
- R$^{II}$, R$^{III}$, R$^{IV}$, an equal to or different from each other and are selected from alkyl and alkoxy groups containing from 1 to 10 carbon atoms; and
- R$^I$ is selected from alkylene, aminoalkylene and aminoalkylarylene groups.

8. The article of manufacture of claim 7 wherein the organic polymer is selected from aromatic polycarbonates, aliphatic polycarbonates, polyacrylates, polymethacrylates, polyesters, cellulose esters, polyacetates, polyamides, polyvinylchloride, polysulphone, polyethersulphone, polystyrene and copolymers of styrene with acrylonitrile and acrylonitrile-butadiene.

9. A substantially transparent laminated article of manufacture comprising at least two sheets of an organic polymer bonded by a thermoplastic adhesive characterized in that at least one of the sheets of organic polymer is coated with an organofunctional siloxane having the formula (I)

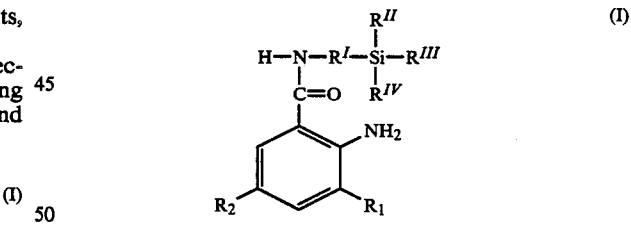

wherein
- R$_1$ and R$_2$ are equal to or different from each other and are selected from Cl, Br, CH$_3$, NO$_2$, H and NH$_2$;
- R$^{II}$, R$^{III}$, R$^{IV}$, an equal to or different from each other and are selected from alkyl and alkoxy groups containing from 1 to 10 carbon atoms; and
- R$^I$ is selected from alkylene, aminoalkylene and aminoalkylarylene groups.

10. The substantially transparent laminated article of manufacture of claim 9, wherein the organic polymer is selected from aromatic polycarbonates, aliphatic polycarbonates, polyacrylates, polymethacrylates, polyesters, cellulose esters, polyacetates, polyamides, polyvinylchloride, polyethersulphone, polystyrene and copolymers of styrene with acrylonitrile and acrylonitrile-butadiene.

* * * * *